United States Patent
Khoshdel et al.

(10) Patent No.: US 10,813,868 B2
(45) Date of Patent: Oct. 27, 2020

(54) METHOD OF IMPROVING HAIR VOLUME

(71) Applicant: Conopco, Inc., Englewood Cliffs, NJ (US)

(72) Inventors: Ezat Khoshdel, Neston (GB); Prem Kumar Cheyalazhagan Paul, Wirral (GB)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

(21) Appl. No.: 15/523,121

(22) PCT Filed: Nov. 2, 2015

(86) PCT No.: PCT/EP2015/075439
§ 371 (c)(1),
(2) Date: Apr. 28, 2017

(87) PCT Pub. No.: WO2016/074966
PCT Pub. Date: May 19, 2016

(65) Prior Publication Data
US 2017/0333328 A1    Nov. 23, 2017

(30) Foreign Application Priority Data
Nov. 13, 2014  (EP) .................................... 14193097

(51) Int. Cl.
| A61K 8/60 | (2006.01) |
| A61K 8/44 | (2006.01) |
| A61Q 5/06 | (2006.01) |
| A61Q 5/00 | (2006.01) |
| A61K 8/362 | (2006.01) |
| A61K 8/365 | (2006.01) |
| A61K 8/37 | (2006.01) |
| A61K 8/67 | (2006.01) |

(52) U.S. Cl.
CPC ............... *A61K 8/60* (2013.01); *A61K 8/362* (2013.01); *A61K 8/365* (2013.01); *A61K 8/37* (2013.01); *A61K 8/44* (2013.01); *A61K 8/675* (2013.01); *A61Q 5/002* (2013.01); *A61Q 5/06* (2013.01)

(58) Field of Classification Search
None
See application file for complete search history.

(56) References Cited

U.S. PATENT DOCUMENTS

| 4,329,338 | A | * | 5/1982 | Szego ................... A61K 8/675 |
| | | | | 514/27 |
| 4,542,014 | A | | 9/1985 | Bresak et al. |

| 2004/0156873 | A1 | * | 8/2004 | Gupta .................. A61K 8/0212 |
| | | | | 424/401 |
| 2004/0166126 | A1 | | 8/2004 | Cannell et al. |
| 2006/0084656 | A1 | | 4/2006 | Ziegler et al. |

FOREIGN PATENT DOCUMENTS

| EP | 0507272 | 6/1992 |
| JP | 2006524187 | 10/2006 |
| WO | WO02078649 | 10/2002 |
| WO | WO02078655 | 10/2002 |
| WO | WO2004068970 | 8/2004 |
| WO | WO2009053163 | 4/2009 |
| WO | WO2013076061 | 5/2013 |
| WO | WO2016074966 | 5/2016 |

OTHER PUBLICATIONS

Trichogen. http://dewolfchem.com/wp-content/uploads/2015/05/Brochure.Trichogen-VEG-UL-LS-9922.02012013.pdf. Published: Mar. 2012.*
Grooming Lounge. https://www.groominglounge.com/best-mens-hair-style-guide-tip. Published: Mar. 4, 2013.*
Ghd. https://www.ghdhair.com/us/articles/the-science-of-drying-your-hair. Published: Mar. 10, 2018.*
Hair & Scalp Stimulating Program, Mintel GNPD, 2011, pp. 1-5 (also cited as XP002738650).
Scalp Revitalizer, Database GNPD online Mintel 2012, 2012, pp. 1-4 (also cited as XP002738651).
Search Report in EP14193096, dated Apr. 20, 2015.
Search Report in EP14193097, dated Apr. 20, 2015.
Search Report in PCTEP2015075439, dated Dec. 8, 2015.
Search Report in PCTEP2015075448, dated Dec. 8, 2015.
Written Opinion in EP14193096, dated Apr. 20, 2015.
Written Opinion in EP14193097, dated Apr. 20, 2015.
Written Opinioin in PCTEP2015075439, dated Dec. 8, 2015.
Written Opinion in PCTEP2015075448, dated Dec. 8, 2015.
Co-Pending Application, Ezat Khoshdel et al., filed Apr. 28, 2017.
Final Effectrs Finishing; Mintel GNPD; 2013; pp. 1-3 (record ID: 2000829.

* cited by examiner

*Primary Examiner* — Nicole P Babson
*Assistant Examiner* — Lori K Mattison
(74) *Attorney, Agent, or Firm* — Foley & Lardner LLP

(57) ABSTRACT

The invention provides a method for improving the volume of hair which comprises the following steps: (i) treating the hair by topical application of a composition comprising from 1 to 25 wt % of one or more glucosamine salts; (ii) shaping the treated hair; (iii) allowing the composition to remain in contact with the shaped hair before drying. Advantageously the method of the invention does not require the breakage of the hair disulfide bonds, does not require the use of high temperature heated implements such as straightening irons, and can be accomplished by a consumer without intervention of a professional hairdresser.

19 Claims, 1 Drawing Sheet

METHOD OF IMPROVING HAIR VOLUME

FIELD OF THE INVENTION

The invention relates to a method for improving the volume of hair.

BACKGROUND AND PRIOR ART

People with fine or thin hair often desire more hair volume, which is the visible bulkiness of hair.

One approach towards increasing hair volume is to use products such as hair styling gels and mousses. During their wet state on hair, gels and mousses help in the creation of a hair style. On drying, a polymeric film forms on the hair, which helps in holding and maintaining the created hair volume. However this effect is often short lived and may be at least partially lost by combing the hair thoroughly. Also, some of the polymers used in these products can leave the hair feeling stiff, tacky or rough.

Other techniques used to increase the appearance of hair volume include perming, back combing, and use of high temperature heated implements such as straightening irons. However, all of these processes can cause a degree of mechanical or chemical damage to the hair if used excessively.

It is an object of the present invention to provide a method for improving the volume of hair without the negatives associated with the prior art methods described above.

Advantageously the method of the invention does not require the breakage of the hair disulfide bonds, does not require the use of high temperature heated implements such as straightening irons, and can be accomplished by a consumer without intervention of a professional hairdresser.

SUMMARY OF THE INVENTION

The invention provides a method for improving the volume of hair which comprises the following steps:
(i) treating the hair by topical application of a composition comprising from 1 to 25 wt % of one or more glucosamine salts;
(ii) shaping the treated hair;
(iii) allowing the composition to remain in contact with the shaped hair before drying.

BRIEF DESCRIPTION OF THE FIGURE

FIG. 1 is an image of a mannequin head taken the day following a test performed with one half (right hand side) treated with water and the other half (left hand side) treated with 2% glucosamine.HCl salt solution and followed by styling with a blow dryer.

DETAILED DESCRIPTION AND PREFERRED EMBODIMENTS

The composition for use in step (i) of the method of the invention comprises from 1 to 25 wt % of one or more glucosamine salts.

Glucosamine is 2-amino-2-deoxy-D-glucose, and is found in chitin, glycoproteins and glycosaminoglycans.

Various cosmetically-acceptable, soluble or sparingly-soluble, inorganic or organic acid salts of glucosamine may be used in the method of the invention. Soluble salts are defined as at least 1 g of salt dissolved per 100 g of solvent at 25° C. Sparingly-soluble salts are defined as from 0.1 to 1 g of salt dissolved per 100 g of solvent at 25° C. Since the compositions used in the method of the invention are usually aqueous-based, the "solvent" in the above context is usually water. Water-soluble inorganic or organic acid salts of glucosamine are preferred for use in the method of the invention.

Examples of inorganic acid salts usable in the present invention can include the sulfate and the hydrochloride, with the hydrochloride being preferred.

Examples of organic acid salts usable in the present invention can include those salts formed between glucosamine and organic acids represented by the formula:

$$R-(COOH)_n$$

wherein n has a value of 1 or 2 and R represents a mono- or divalent organic radical composed of carbon, hydrogen and optionally at least one of oxygen, nitrogen and sulfur.

Preferred acids are mono- and dicarboxylic acids composed of carbon, hydrogen, oxygen and nitrogen.

Illustrative organic acid salts usable in the present invention include organic monocarboxylic acid salts corresponding to the following general formula (I):

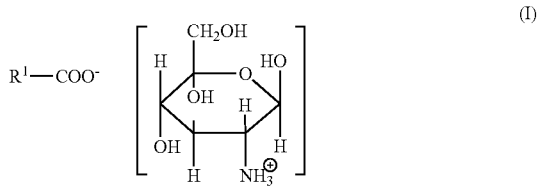

in which $R^1$ is a monovalent, saturated or unsaturated, linear or branched aliphatic chain having from 1 to 6, preferably 1 to 3 carbon atoms, which may optionally be substituted with one or more hydroxyl or amino groups;

or a monovalent aromatic group with a 5 carbon or 6 carbon ring;

or a monovalent cycloheteroaliphatic group with a 5 atom or 6 atom ring and in which there are 1 to 4 heteroatoms selected from N and O;

or a monovalent heteroaromatic group with a 5 atom or 6 atom ring and in which there are 1 to 4 heteroatoms selected from N and O.

The above aromatic, cycloheteroaliphatic or heteroaromatic groups can optionally be substituted with one or more substituents selected from halogen, oxy, hydroxy, imino, amino, $C_1$-$C_4$ alkyl and $C_1$-$C_4$ alkoxy groups.

Organic acid salts usable in the present invention can also include organic dicarboxylic acid salts corresponding to the following general formula (II):

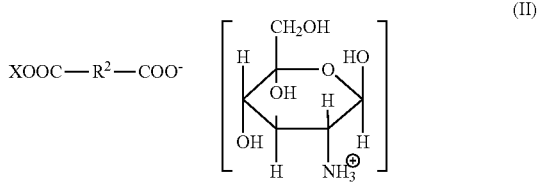

in which $R^2$ is a divalent, saturated or unsaturated, linear or branched aliphatic chain having from 1 to 8 carbon atoms, which may optionally be substituted with one or more hydroxyl or amino groups;
and in which X is selected from H and

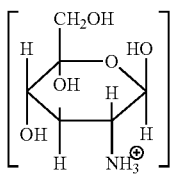

Preferably R² is a saturated or monounsaturated linear aliphatic chain having from 1 to 5 carbon atoms, optionally with an amino (—NH₂) substituent.

Preferably X is

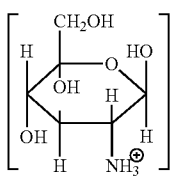

Examples of preferred organic acid salts usable in the present invention include glucosamine pimelate, glucosamine glutarate, glucosamine succinate, glucosamine malonate, glucosamine fumarate, glucosamine maleate, glucosamine glutamate, glucosamine aspartate, glucosamine lactate, glucosamine glycinate, glucosamine nicotinate, glucosamine 2-pyrrolidone-5-carboxylate, diglucosamine pimelate, diglucosamine adipate, diglucosamine glutarate, diglucosamine succinate, diglucosamine malonate, diglucosamine fumarate, diglucosamine maleate, diglucosamine glutamate and diglucosamine aspartate.

Particularly preferred organic acid salts usable in the present invention are glucosamine glycinate, glucosamine nicotinate, glucosamine 2-pyrrolidone-5-carboxylate, diglucosamine glutarate, diglucosamine fumarate, diglucosamine glutamate and diglucosamine aspartate.

Mixtures of any of the above described materials may also be used.

The organic acid salts described above may typically be prepared by obtaining the glucosamine base from glucosamine hydrochloride, and subsequently adding the corresponding acid, depending on the salt it is desired to obtain. Glucosamine base is generally obtained by treating glucosamine hydrochloride with triethylamine, or with sodium methoxide, or alternatively by means of anionic exchange resins. The salts may also be directly obtained from glucosamine hydrochloride, using an anionic exchange resin previously conditioned with the acid containing the anion of the salt it is desired to obtain. If the organic acid contains more than one carboxyl group, then the salt obtained may be selected by varying the starting quantity of glucosamine or glucosamine hydrochloride.

Preferably the level of glucosamine salt (s) ranges from 1 to 5 wt % and more preferably from 1 to 3 wt %, by weight based on the total weight of the composition.

Advantageously, the method of the invention does not require the breakage of hair disulfide bonds, and compositions for use in the invention do not require the incorporation of reducing agents.

Accordingly, compositions for use in step (i) of the method of the invention are generally substantially free of reducing agents. The term "substantially free" in the context of this invention means that reducing agents are absent or included in trace quantities only, such as no more than 0.1 wt %, preferably no more than 0.01 wt %, and more preferably from 0 to 0.001 wt % (by weight based on the total weight of the composition).

The term "reducing agent" in the context of this invention means an agent which is effective to break hair disulfide bonds when applied to hair for a period ranging from about 3 to 15 minutes and at a temperature ranging from about 20 to 30° C. Examples of such reducing agents are ammonium thioglycolate (in a solution having a pH of between about 7 and 10.5), glyceryl monothioglycolate (employed at a pH of less than 7), thioglycolic acid, dithioglycolic acid, mercaptoethyl amine, mercaptopropionic acid, dithioglycolate and alkali metal or ammonium sulfites or bisulfites.

Compositions for use in step (i) of the method of the invention will generally comprise at least 60 wt %, preferably at least 70 wt % and more preferably at least 80 wt % water (by weight based on the total weight of composition). Preferably, the composition comprises no more than 99 wt % and more preferably no more than 98 wt % water (by weight based on the total weight of the composition). Other organic solvents may also be present, such as lower alkyl alcohols and polyhydric alcohols. Examples of lower alkyl alcohols include $C_1$ to $C_6$ monohydric alcohols such as ethanol and isopropanol. Examples of polyhydric alcohols include propylene glycol, hexylene glycol, glycerin, and propanediol.

Mixtures of any of the above described organic solvents may also be used.

Compositions for use in step (i) of the method of the invention may suitably have a conditioning gel phase, which may be generally characterized as a gel (Lβ) surfactant mesophase consisting of surfactant bilayers. Such a conditioning gel phase may be formed from a cationic surfactant, a high melting point fatty alcohol and an aqueous carrier. Typically these components are heated to form a mixture, which is cooled under shear to room temperature. The mixture undergoes a number of phase transitions during cooling, normally resulting in a gel (L_β) surfactant mesophase consisting of surfactant bilayers.

Examples of suitable cationic surfactants which are useful for forming the conditioning gel phase include quaternary ammonium cationic surfactants corresponding to the following general formula:

$$[N(R^1)(R^2)(R^3)(R^4)]^+ \ (X)^-$$

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably $CH_3$.

Specific examples of such preferred quaternary ammonium cationic surfactants for use in forming the conditioning gel phase are cetyltrimethylammonium chloride (CTAC), behenyltrimethylammonium chloride (BTAC) and mixtures thereof.

Mixtures of any of the above-described cationic surfactants may also be suitable.

The level of cationic surfactant suitably ranges from 0.1 to 10 wt %, preferably from 0.2 to 5 wt % and more preferably from 0.25 to 4 wt % (by total weight of cationic surfactant based on the total weight of the composition).

By "high melting point" in the context of this invention is generally meant a melting point of 25° C. or higher. Generally the melting point ranges from 25° C. up to 90° C., preferably from 40° C. up to 70° C. and more preferably from 50° C. up to about 65° C.

The high melting point fatty alcohol can be used as a single compound or as a blend or mixture of at least two high melting point fatty alcohols. When a blend or mixture of fatty alcohols is used, the melting point means the melting point of the blend or mixture.

Suitable fatty alcohols of this type have the general formula R—OH, where R is an aliphatic carbon chain. Preferably R is a saturated aliphatic carbon chain comprising from 8 to 30 carbon atoms, more preferably from 14 to 30 carbon atoms and most preferably from 16 to 22 carbon atoms.

R can contain, in addition to carbon and hydrogen atoms, ether linkages, and other groups such as amino groups.

Most preferably, the fatty alcohol has the general formula $CH_3(CH_2)_nOH$, where n is an integer from 7 to 29, preferably from 15 to 21.

Specific examples of suitable fatty alcohols are cetyl alcohol, stearyl alcohol, behenyl alcohol, and mixtures thereof. Cetyl alcohol, stearyl alcohol and mixtures thereof are particularly preferred.

Mixtures of any of the above-described fatty alcohols may also be suitable.

The level of fatty alcohol suitably ranges from 0.01 to 10 wt %, preferably from 0.1 to 8 wt %, more preferably from 0.2 to 7 wt % and most preferably from 0.3 to 6 wt % (by weight based on the total weight of the composition).

The weight ratio of cationic surfactant to fatty alcohol is suitably from 1:1 to 1:10, preferably from 1:1.5 to 1:8, optimally from 1:2 to 1:5.

The composition may also incorporate other optional ingredients to enhance performance and/or consumer acceptability. Suitable optional ingredients include: preservatives, colouring agents, chelating agents, antioxidants, fragrances, antimicrobials, antidandruff agents, cationic conditioning polymers, styling ingredients, sunscreens, proteins and hydrolysed proteins.

Preferably, the composition is a single dose composition. The term "single dose" in the context of this invention means that the composition is to be topically applied to the hair in one go.

Preferably, the composition is topically applied to the hair at a temperature from 15 to 40° C., and more preferably at a temperature from 20 to 30° C.

Preferably, the composition is applied to dry hair. The term "dry hair" in the context of this invention generally means hair from which free water (i.e. water disposed as a film or droplets on the cuticle surface) has been substantially removed. Hair may be dried by exposure to air, by use of a heated hair drying appliance, by rubbing with a water-absorbent article, or by a combination of any of these methods. Preferably, the dry hair will not have been washed or actively wetted, (such as by shampooing, conditioning, rinsing or otherwise treating with an aqueous composition) in the preceding 2 hours and more preferably in the preceding 3 hours prior to topical application of the composition in accordance with step (i) of the method of the invention, and will have been permitted to acclimatise to atmospheric conditions. In such circumstances there is substantially no free water present which interferes with the adsorption of the composition on application. A suitable indicator of dry hair in the context of this invention would be a hair fibre whose calculated water content does not exceed 25 wt % by weight based on the total weight of the hair fibre.

In step (ii) of the method of the invention, the treated hair is shaped.

Shaping of the hair in the method of the invention can be accomplished by such means as the finger tips, a plastic hair pick or the tail of a comb, the shaping being performed on portions of the hair comprising strands of hair in various numbers. Using such means, the hair may, according to individual tastes, be lifted in straight form, or shaped gently, for example, into bends, waves or curls. If desired, plastic clips may be employed. In the case of long hair, the hair can be loosely piled on top of the head.

A hot tool, such as a flat hair iron or hand-held hair dryer, may be used in the hair shaping step. Such tools apply high levels of heat directly to the hair. Most operate in the 45° C. to 250° C. range, and are usually employed at temperature settings ranging from 50° C. to about 220° C., depending on the particular tool.

However, the use of hot tools is not essential in the method of the invention. This is especially advantageous for consumers who wish to reduce or avoid the exposure of their hair to high temperatures, for example if their hair is fragile or overprocessed from previous chemical treatments such as bleaching and perming.

Accordingly the shaping of the hair in step (ii) of the method of the invention is preferably conducted at a temperature from 15 to 60° C., more preferably at a temperature from 20 to 40° C.

Most preferably in step (ii) of the method of the invention the hair is shaped by combing it into a straightened configuration at a temperature from 20 to 40° C.

In step (iii) of the method of the invention, the composition is allowed to remain in contact with the shaped hair before drying.

Preferably the composition is allowed to remain in contact with the shaped hair until the hair is dry.

The hair may be dried naturally by exposure to air, by use of a heated hair drying appliance, by rubbing with a water-absorbent article, or by a combination of any of these methods.

The composition may thus remain in contact with the shaped hair for a period of at least about 3 minutes up to 3 hours or more if the hair is allowed to dry naturally.

The dried hair may be re-shaped if desired, such as by combing it into a straightened configuration at a temperature from 20 to 40° C.

The composition may then be rinsed from the hair at the next wash.

The invention is further illustrated with reference to the following, non-limiting Examples.

All ingredients are expressed by weight percent of the total formulation, and as level of active ingredient.

EXAMPLES

All ingredients are expressed by weight percent of the total formulation, and as level of active ingredient.

Example 1a

Dark brown European wavy #6 switches (from 2 different batches) of length 25 cm and weight 2 g were dosed with 0.2 ml each of 2% glucosamine.HCl salt solution. Control switches were wetted with water. All switches were combed straight and left to dry overnight. When dry the switches were combed straight and pictures taken. The volume of the switches shows the volumising benefit of the technology. (Here volume refers to the projection of the switch image on to the screen and is given in $mm^2$).

The results are shown in Table 1 below.

TABLE 1

| Treatment | Batch 1 volume | Batch 1 % benefit | Batch 2 volume | Batch 2 % benefit |
|---|---|---|---|---|
| water | 13347 | 0 | 15705 | 0 |
| 2% glucosamine•HCl | 14236 | 6.7 | 16851 | 7.3 |

The results show that for both batches of switches, the volumising benefit of the treatment with glucosamine salt (according to the method of the invention) is c.7%.

Example 1b

A half head test on a mannequin head was performed with one half (right hand side) treated with water and the other half (left hand side) treated with 2% glucosamine.HCl salt solution. The head was styled with a blow dryer for volume up benefit.

FIG. 1 is a picture taken the day following the styling. The volumising benefit of the treatment with glucosamine salt (according to the method of the invention) is clearly evident from a visual comparison between the right hand side and the left hand side of the mannequin head.

Example 2

Dark brown European wavy #6 switches of length 25 cm and weight 2 gms (from the same batch of switches), were dosed with 0.2 ml each of 2% solutions of various mono and diglucosamine salts. Control switches were treated with water.

All switches were combed straight and left to dry overnight.

When dry the switches were combed straight and pictures taken. The volume of the switches shows the volumising benefit of the technology. (Here volume refers to the projection of the switch image on to the screen and is given in $mm^2$). The percentage benefit (i.e. increase in volume) with respect to control (water) is also given.

The results are shown in Table 2.

TABLE 2

| Treatment | Volume $mm^2$ | % benefit |
|---|---|---|
| Water (control) | 14182 | 0.0 |
| glucosamine pimelate | 16088 | 13.4 |
| glucosamine glutarate | 15475 | 9.1 |
| glucosamine succinate | 16102 | 13.5 |
| glucosamine malonate | 17244 | 21.6 |
| glucosamine fumarate | 16802 | 18.5 |
| glucosamine maleate | 18450 | 30.1 |
| glucosamine glutamate | 18563 | 30.9 |
| glucosamine aspartate | 18566 | 30.9 |
| glucosamine lactate | 18944 | 33.6 |
| glucosamine glycinate | 19748 | 39.2 |
| glucosamine nicotinate | 20087 | 41.6 |
| glucosamine PCA | 19505 | 37.5 |
| diglucosamine pimelate | 18021 | 27.1 |
| diglucosamine adipate | 18189 | 28.3 |
| diglucosamine glutarate | 19234 | 35.6 |
| diglucosamine succinate | 17136 | 20.8 |
| diglucosamine malonate | 19053 | 34.3 |
| diglucosamine fumarate | 19575 | 38.0 |
| diglucosamine maleate | 19053 | 34.3 |
| diglucosamine glutamate | 19575 | 38.0 |
| diglucosamine aspartate | 19780 | 39.5 |

The results show that treatment with glucosamine salts (according to the method of the invention) gives excellent hair volumising benefit.

The invention claimed is:

1. A method for improving the volume of hair comprising:
   (i) treating the hair by topical application of a composition comprising from 1 to 25 wt % of one or more glucosamine organic acid salts represented by Formula (II):

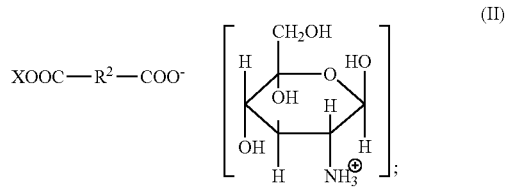

(ii) shaping the treated hair; and
   (iii) allowing the composition to remain in contact with the shaped hair until the hair is dry;
   wherein:
   $R^2$ is a 1 to 8 carbon divalent, saturated or unsaturated, linear or branched aliphatic chain, optionally substituted with one or more hydroxyl or amino groups;
   X is H or

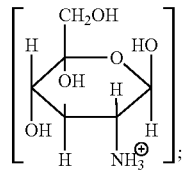

and the method increases the volume (mm²) of the treated hair relative to the volume of hair treated with water.

2. The method of claim 1, wherein the one or more glucosamine organic acid salts are selected from the group consisting of diglucosamine pimelate, diglucosamine adipate, diglucosamine succinate, diglucosamine malonate, diglucosamine glutarate, diglucosamine fumarate, diglucosamine glutamate, diglucosamine aspartate and mixtures thereof.

3. The method of claim 1, wherein the composition further comprises from 0 to 0.001 wt % reducing agents based on the total weight of the composition.

4. The method of claim 1, wherein the hair is shaped by combing it into a straightened configuration at a temperature from 20 to 40° C.

5. The method of claim 1, wherein the composition comprises 1 wt % to 5 wt % of the one or more glucosamine organic salts based on the total weight of the composition.

6. The method of claim 5, wherein the composition comprises 1 wt % to 3 wt % of the one or more glucosamine organic salts based on the total weight of the composition.

7. The method of claim 1, wherein R² is a 1 to 5 carbon divalent, saturated or monosaturated linear aliphatic chain, optionally substituted with an amino substituent.

8. The method of claim 1, wherein X is

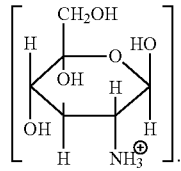

9. The method of claim 2, wherein the one or more glucosamine organic acid salts are selected from the group consisting of diglucosamine pimelate, diglucosamine glutarate, diglucosamine fumarate, diglucosamine glutamate, diglucosamine aspartate and mixtures thereof.

10. The method of claim 1, wherein the shaping further comprises shaping the treated hair with a hot tool at a temperature from 45° C. and 250° C.

11. The method of claim 1, wherein the method increases the volume of the treated hair from about 9% to about 42% relative to the volume of hair treated with water.

12. A method for improving the volume of hair comprising:
(i) treating the hair by topical application of a composition comprising from 1 to 25 wt % of one or more glucosamine organic acid salts selected from the group consisting of diglucosamine pimelate, diglucosamine adipate, diglucosamine succinate, diglucosamine malonate, diglucosamine glutarate, diglucosamine fumarate, diglucosamine glutamate, diglucosamine aspartate and mixtures thereof;
(ii) shaping the treated hair; and
(iii) allowing the composition to remain in contact with the shaped hair before drying; wherein the method increases the volume (mm²) of the treated hair relative to the volume of hair treated with water.

13. The method of claim 11, wherein the composition further comprises from 0 to 0.001 wt % reducing agents based on the total weight of the composition.

14. The method of claim 11, wherein the hair is shaped by combing it into a straightened configuration at a temperature from 20 to 40° C.

15. The method of claim 11, wherein the composition is allowed to remain in contact with the shaped hair in step (iii) until the hair is dry.

16. The method of claim 11, wherein the composition comprises 1 wt % to 5 wt % of the one or more glucosamine organic salts based on the total weight of the composition.

17. The method of claim 15, wherein the method increases volume of the treated hair by about 9% to about 42% relative to the volume of hair treated with water.

18. The method of claim 11, wherein the one or more glucosamine organic acid salts are selected from the group consisting of diglucosamine pimelate, diglucosamine glutarate, diglucosamine fumarate, diglucosamine glutamate, diglucosamine aspartate and mixtures thereof.

19. A method for improving the volume of hair comprising:
(i) treating the hair by topical application of a composition comprising from 1 to 25 wt % of one or more glucosamine organic acid salts represented by Formula (II):

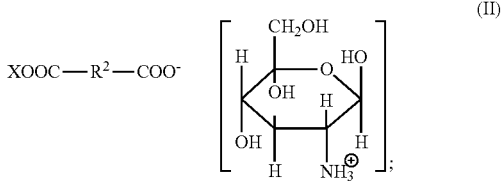

(ii) shaping the treated hair; and
(iii) allowing the composition to remain in contact with the shaped hair before drying;
wherein:
R² is a 1 to 5 carbon divalent, saturated or monosaturated linear aliphatic chain, optionally substituted with an amino substituent;
X is

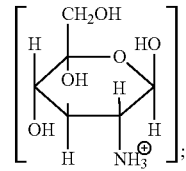

and
the method increases the volume (mm²) of the treated hair relative to the volume of hair treated with water.

* * * * *